United States Patent [19]

Graham et al.

[11] Patent Number: 4,808,926
[45] Date of Patent: Feb. 28, 1989

[54] EDDY CURRENT APPARATUS AND METHOD FOR CONTROLLING A ROD MILL ON THE BASIS OF FAULTS DETECTED PER UNIT TIME

[75] Inventors: Randall C. Graham, Nashville; James D. Smith, Jr., Fairview, both of Tenn.

[73] Assignee: Essex Group, Inc., Fort Wayne, Ind.

[21] Appl. No.: 897,226

[22] Filed: Aug. 18, 1986

[51] Int. Cl.⁴ .................. G01N 27/90; B21B 37/00; B21C 51/00; G01D 9/00

[52] U.S. Cl. .................. 324/226; 72/10; 72/33; 324/240; 324/241; 346/33 F; 364/472; 364/507; 377/20

[58] Field of Search .............. 324/202, 226, 228–243; 72/10, 31, 33, 43; 73/159, 160; 340/675–677, 526; 346/33 F; 364/472, 507; 377/19, 20

[56] References Cited

U.S. PATENT DOCUMENTS

| | | | |
|---|---|---|---|
| 2,889,513 | 6/1959 | Callan et al. | 324/202 |
| 3,262,123 | 7/1966 | Crouch | 324/240 X |
| 3,823,370 | 7/1974 | Pendleton et al. | 324/515 |
| 3,904,957 | 9/1975 | Griese | 324/233 |
| 3,983,371 | 9/1976 | Siranni et al. | 324/226 X |
| 4,167,004 | 9/1979 | Schenck et al. | 340/679 |
| 4,209,744 | 6/1980 | Gerasimov et al. | 324/241 |
| 4,399,354 | 8/1983 | Schaeffer | 377/20 X |
| 4,615,195 | 10/1986 | Vogel et al. | 72/43 X |

Primary Examiner—Gerard R. Strecker
Attorney, Agent, or Firm—Francis J. Maguire, Jr.

[57] ABSTRACT

Method and apparatus for monitoring a rod mill and flexible wire drawn and annealed from a stiff coil of rod in the rod mill are disclosed. The fault signals provided by an eddy-current tester are counted on a per unit time basis in order to permit the detection of rod mill problems before serious deterioration of the mill occurs. This is accomplished by direct observation of an increasing rate of fault signal occurrence. A totalized fault signal count is also provided to aid in detecting low quality wire. This is accomplished by direct observation of uniformly high levels of fault signals. A control function is disclosed whereby the rod mill is shutdown in the presence of a high rate of increase in fault signal occurrences. A "change coil" message may be sent upon detecting uniformly high levels of faults. Fault signals are stored and identified for purposes of traceability. The invention is broadly applicable in other eddy-current testing contexts, that is, other than that context specifically disclosed for the best mode embodiment.

22 Claims, 6 Drawing Sheets

ROD MILL DATA

TIME: 14:11:     GAGE: 10     DATE: 04/10/
DIP IN: 000     FAT %: 01.20     DIP OUT: 000
SUPPLIER: SOUTHWIRE     COIL #: 006071023
WIRE SPEED: 4747     BAR CODE #: 955

| PASS | MAJ | MIN | EPM MAJ | EPM MIN |
|---|---|---|---|---|
| 001 | 0177 | 0307 | 0177 | 0307 |
| 002 | 0447 | 0781 | 0270 | 0474 |
| 003 | 0696 | 1239 | 0249 | 0458 |
| 004 | 0982 | 1711 | 0286 | 0472 |
| 005 | 1278 | 2184 | 0296 | 0473 |
| 006 | 1568 | 2650 | 0290 | 0466 |
| 007 | 1853 | 3121 | 0285 | 0471 |
| 008 | 2080 | 3588 | 0227 | 0467 |
| 009 | 2309 | 4033 | 0229 | 0445 |
| 010 | 2517 | 4476 | 0208 | 0443 |
| 011 | 2719 | 4900 | 0202 | 0424 |
| 012 | 2955 | 5372 | 0236 | 0472 |
| 013 | 3204 | 5839 | 0249 | 0467 |
| 014 | 3422 | 6308 | 0218 | 0469 |
| 015 | 3617 | 6770 | 0195 | 0462 |
| 016 | 3815 | 7234 | 0198 | 0464 |
| 017 | 3978 | 7691 | 0163 | 0457 |
| 018 | 4072 | 8100 | 0094 | 0409 |
| 019 | 4208 | 8539 | 0136 | 0439 |
| 020 | 4373 | 8978 | 0165 | 0439 |
| 021 | 4556 | 9430 | 0183 | 0452 |
| 022 | 4707 | 9884 | 0151 | 0454 |
| 023 | 4908 | —— | 0201 | 0473 |
| 024 | 5092 | —— | 0184 | 0440 |
| 025 | 5328 | —— | 0236 | 0486 |
| 026 | 5637 | | 0309 | 0479 |
| 027 | 5949 | | 0312 | 0478 |
| 028 | 6226 | | 0277 | 0477 |
| 029 | 6441 | | 0215 | 0475 |
| 030 | 6713 | | 0272 | 0477 |
| 031 | 6953 | | 0240 | 0477 |
| 032 | 7163 | | 0210 | 0471 |
| 033 | 7525 | | 0362 | 0476 |
| 034 | 7794 | | 0269 | 0467 |
| 035 | 8011 | | 0217 | 0464 |

EDDY CURRENT APPARATUS AND METHOD FOR CONTROLLING A ROD MILL ON THE BASIS OF FAULTS DETECTED PER UNIT TIME

TECHNICAL FIELD

This invention relates to the manufacture of rod or wire and particularly to a method and apparatus for improving the efficiency of such processes while at the same time improving the quality of the product.

BACKGROUND ART

Eddy-current testers have been in use for many years for testing manufactured rod or wire. For instance, the Institut Dr. Forster of West Germany makes several models of eddy-current testers presently in use. Such testers typically provide, at an output thereof, a fault signal whenever a disturbance in eddy-currents within a test piece indicates a flaw or defect in the rod or wire. The fault signals may typically be of two types, i.e., major and minor. These signals are sometimes provided to a CRT display (see, for example, FIG. 3 of U.S. Pat. No. 3,904,957) for continuous visual monitoring, to a defect counter for providing a total defect count (see Column 1, line 40 of U.S. Pat. No. 3,904,957), or to a stripchart recorder upon which a pen inscribes a horizontal line which provides a spike in the presence of a fault. The defect counter is useful for viewing, from time to time, the total number of faults which have occurred so far in a workpiece and hence, its overall quality. However, the defect counter is not useful for indicating the rate of increase of faults unless viewed more or less continually. Knowledge of the rate of increase is useful for other purposes, to be described subsequently herein.

In the stripchart recorder approach, the stripchart is rolled up on a cylinder for later viewing by unrolling the paper periodically for evaluation. Two pens may be provided for providing two horizontal lines, one for major, and the other for minor faults. This method of recording data generates a considerable amount of paper. The operator must manually sort through and count all the faults in order to come to any useable conclusions concerning the quality of the product. If the operator should desire to determine the rate of increase of fault signals he is faced with the twin difficulties of having to unroll the unwieldy paper and at the same time attempt to qualitatively determine the rate of increase by inspection. A quantitative measurement is not available except by painstaking manual measurement and calculation. Furthermore, the equipment provided is typically not only very expensive but it requires considerable expenditure of man-hours to correlate data.

DISCLOSURE OF THE INVENTION

An object of the present invention is to provide a method and means for efficiently counting and displaying eddy-current fault signals. Another object of the present invention is to display such fault signals on a per unit time basis so that the operator may quickly form conclusions concerning both the quality of a supplier's stock, e.g., a rod coil, presently being worked, e.g., drawn, and the integrity of the working device, e.g., a rod mill, itself. Another object of the present invention is to provide traceability in manufactured product, e.g., rod or wire, back to the original supplier of worked stock, e.g., rod coil, even to the particular piece, e.g., rod coil. Another object of the present invention is to provide a method and means for actually automatically controlling the working device, e.g., rod mill to cause a shutdown in the presence of an increasing rate of fault signals above a selected, maximum acceptable rate of increase. Another object of the present invention is to provide a "change stock," e.g., a "change coil" signal for display in the presence of a total fault signal count greater than a maximum acceptable level so that the operator may be advised by an appropriate display that it is time to replace the present stock, e.g., coil, feeding the working device, e.g., rod mill, with new stock, e.g., a new coil, since at the present fault level the stock, or coil, is deemed to be defective.

It will be understood by those skilled in the art that although the invention disclosed and claimed herein is semantically limited to a wire manufacturing process in which rod coil stock is drawn and annealed in a rod mill to produce wire, the semantic limitation is not intended by the inventors to limit the scope of their invention to the particular process disclosed. It is widely applicable to any similar eddy-current testing of any workpiece produced in any working device from any stock. Therefore, the following disclosure of invention, drawing, best mode description and claims should be read with this delimitation in mind.

In accordance with the present invention, a method and apparatus for monitoring a rod mill and wire drawn from a coil of rod input to the rod mill comprises the steps, which may be carried out by the apparatus claimed herein, of eddy-current testing the wire drawn in the rod mill and providing fault signals in the presence of tested faults; counting the number of fault signals provided on a per unit time basis and providing a count signal indicative of the separate magnitudes thereof; and displaying the magnitudes of said count signals provided on a per unit time basis.

In further accord with the present invention, the counted number of fault signals are totalized and displayed to indicate the magnitude of the totalized count signal.

In still further accord with the present invention, the count signals may be stored for later evaluation. Such evaluation may include much delayed tracing of customer reported defective wires back to particular coils from particular suppliers. It may also include evaluating data for determining acceptable fault levels.

In still further accord with the present invention, the stored count signals may have other associated signals stored with them including signals identifying the supplier of the coil, identifying the percent fat presently in a lubricant sprayed on rod in drawing dies in the rod mill, or rod coil identifying signals which may include bar codes.

In still further accord with the present invention, the fault signals may be characterized as either major or minor wherein each type is counted and displayed separately.

In still further accord with the present invention, the count of the fault signals may be displayed in tabular form or, they may be displayed in bargraph form, or both.

In still further accord with the present invention, the present rate of increase of a count signal magnitude may be determined in order to compare the present magnitude of the rate of increase to a reference level indicating a maximum acceptable level, and providing a rod mill shutdown signal in the presence of the rate of increase being greater than the maximum acceptable level.

In still further accord with the present invention, the magnitude of the totalized count signal may be compared to a selected signal magnitude above which a "change coil" signal is provided to the display in order to enable the operator to change a coil which is deemed to be defective.

The present invention provides a different approach than the simple total defect counter method of eddy-current testing. And no longer is the cumbersome strip-chart recorder method required for evaluation purposes. The prior art method of examining great lengths of paper on rolls in order to manually examine and count the number of faults has been replaced with an inexpensive, more quantitative and more effective digital method and apparatus.

Furthermore, the digital method permits fault signals to be counted on a per unit time basis which has great significance in determining whether or not the working device, e.g., the rod mill is deteriorating in some operational aspect. This is a totally new function provided by eddy-current testing in that the prior art merely provided a means for laboriously counting faults at a time subsequent to the actual occurrence thereof. This function was directed toward determining the quality of the stock used at the input of the manufacturing process rather than to the process itself. The present invention permits immediate and rapid identification of not only the number of counted faults, indicating a problem with the quality of the stock, as in the prior art, albeit more laboriously, but also permits the identification of a rate of increase of fault signals indicative of a problem with the working device, e.g., the rod mill itself. (Quick identification of a rod mill problem is highly advantageous in that it permits shutdown thereof before serious damage occurs therein, e.g., bearings).

The present method and apparatus also provide the highly desireable ability to identify particular coils uniquely according to supplier and coil number. This permits traceability of the product in case a customer comes back and indicates that a particular spool of wire is defective. By enabling the manufacturer to identify the particular coil, the supplier can be notified of the problem which helps him to improve his process.

In addition, the wire manufacturer can now go back and check the total count signal levels recorded for that particular coil and use that information to adjust the acceptability level of counts for rejecting coils before shipment to customers.

Furthermore, the present invention permits the storage of other information entered at the time of manufacture along with the count signals. For example, one may store the percent fat information concerning the amount of fat being sprayed on the dies at the time of manufacture. If, for example, there is a lubricant problem identified later, one may go back to the stored vaules of percent fat to determine whether certain levels of percent fat produce more or less faults than others. This helps to improve quality over the long run. Of course, other parameters may similarly be stored for the same purpose of quality improvement.

These and other objects, features and advantages of the present invention will become more apparent in light of the detailed description of a best mode embodiment thereof, as illustrated in the accompanying drawing.

BEST MODE FOR CARRYING OUT THE INVENTION

Figure 1:
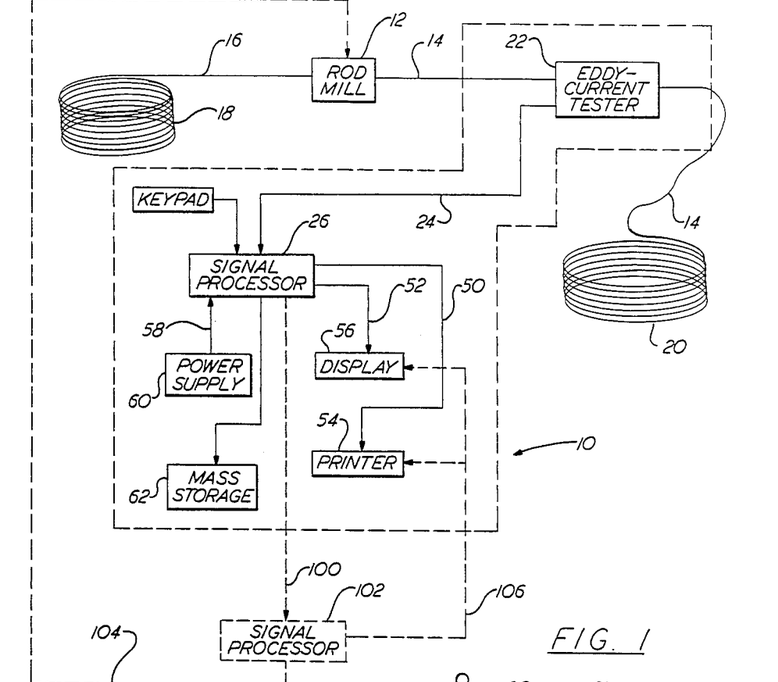
FIG. 1 is a simplified block diagram illustration of an apparatus 10 for carrying out the eddy-current testing and data correlation functions disclosed herein for testing rod stock, wire and a rod mill.

FIG. 1 is an illustration of an apparatus 10, according to the present invention, for monitoring a rod mill 12 and the flexible copper wire 14 made therein from stiff copper rod 16. The rod 16 is typically supplied in coils 18 from various suppliers and may have a thickness of, for example, 10 millimeters. Of course, the principles disclosed herein are widely applicable to any rod thickness. The rod is pulled into the rod mill 12 onto a pair of sheaves. It is then provided to an intake die of the rod mill just before being introduced into a "mud box" which consists of a container of animal fat or grease. After being greased, the rod is presented to a "die box" which may include various selectable sizes of drawing dies. A die is selected according to the desired gauge flexible wire desired on the output of the mill.

All dies must be continuously sprayed to keep them slippery. They are sprayed with a "dip flow" lubricant. This prevents the wire from breaking. The dip flow consist of animal fats and water and other chemicals to keep the fat in solution.

After exiting the die box, the drawn wire goes up to the top of the rod mill where it begins an annealing process by having passed many thousands of electrical amperes through about a hundred feet of the wire to ground. This superheats the wire, which is then travelling at about 25–30 meters per second.

After having the electrical current passed therethrough, the wire is gradually cooled for a period of time with a steam tube until it is rapidly cooled in quench water. The wire is then passed through an "elephant trunk" which spins annealed wire 4 into a coil 20 into a basket (not shown).

An eddy-current tester 22, such as is sold by the Institut Dr. Friedrich Forster Prufgeratebau GmbH & Co., KG, Reutlingen, Federal Republic of Germany, e.g., the DEFECTOMAT model C 2.820, is provided which provides one or more types of fault signals as indicated by a line 24, to a signal processor 26.

Figure 12:
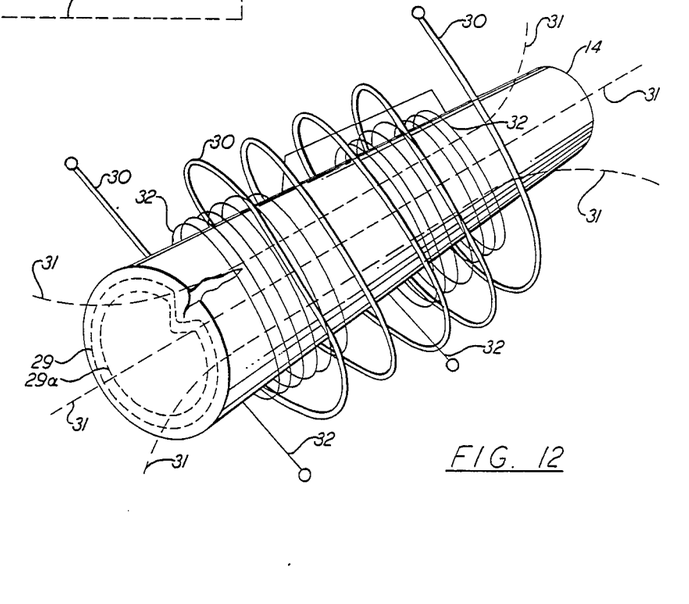
FIG. 12 is an illustration of a wire 14 being passed through a primary 30 and secondary coil 32 in an eddy-current tester.

Referring now to FIG. 12, the eddy-current tester 2 of FIG. 1 operates on the principle that an alternating magnetic field in the vicinity of a wire will induce eddy-currents 29, 29a to a certain depth of the surface thereof which may be measured by a pick-up coil which can detect inhomogeneities in the wire by measuring disturbances in the induced currents.

An alternating current of predetermined frequency flows through a primary coil 30 and produces an alternating magnetic field 31 in its vicinity. A secondary coil 32 is located within the effective area of this alternating field. Depending on the particular design, the secondary coil system is either a difference coil winding or a difference coil winding and an absolute coil winding.

The method of operation will be described in a simplified manner by reference to the difference arrangement shown in FIG. 12 with two secondary windings connected in series opposition.

These windings are matched to each other so that when the test coils are empty, equal voltages are induced in the individual secondary windings, thus giving a difference voltage of zero.

The voltages induced in the windings are complex values, i.e., they are identified by magnitude and phase. A representation of these values in the complex voltage plane would show that the magnitudes are equal and the phase positions of the two voltages are 180° apart.

If now, however, an electrically-conductive piece of metal i.e., the test piece, in this case a wire 14, is placed in the test coils, certain electrical changes take place depending on the properties of the metal. Eddy-currents 29, 29a form at the surface of the test piece according to the excitation frequency. The higher the frequency the less the penetration depth of the eddy-currents. In turn, the eddy-currents produce a secondary alternating magnetic field which opposes the original alternating field and weakens it. The voltages now induced in the secondary windings are smaller in magnitude and displaced from the original phase position (only applies to nonferromagnetic materials; with ferromagnetic metals there can be an increase in the voltages depending on the diameter and frequency).

The spread of the eddy-currents depends on various factors, mainly the frequency of the excitation voltage, but also the electrical conductivity and permeability of the metal test piece. For the purposes of this description the frequency can be assumed constant.

The electrical conductivity of the metal test piece is considerably influenced by inhomogeneities in the material, e.g., cracks, surface voids, laps, etc. Such discontinuities in the material causes a local reduction in the electrical conductivity. The electrical currents cannot form so strongly at such flaws as at points where the material condition is good.

The following can be deduced from the foregoing: if a completely homogeneous, and therefore flawless, metal test piece is placed in the test coils the magnitude and phase of the voltages induced in the individual secondary windings change. These changes, however, are identical in both windings; thus, the resulting difference voltage is again equal to zero as when the test coils are empty.

The situation is different, however, when an inhomogeneous section of material containing a crack is inserted in the test coils, as shown in FIG. 12. If, for example, the crack is within one of the secondary windings but the other secondary winding contains the adjacent flawless section of material, the eddy-current distribution in the two sections of material is different. Consequently, different amounts of field weakening also occur; the voltages induced in the two secondary windings in this case are different. The resulting difference voltage is not zero and indicates the size and properties of the detected flaw.

The method of operation of such an eddy-current tester is well known in the art and reference is made to U.S. Pat. Nos. 3,875,502, 3,896,646, 3,898,556, 3,904,957, 3,980,884, 3,988,665, 4,016,487, 4,063,159, 4,117,403, 4,314,203, 4,331,920, 4,387,338, 4,445,088, 4,447,778, 4,519,243, 4,562,349, 4,566,585, 3,343,079, 3,394,303, 3,895,290, 3,528,003, 3,538,433, 4,167,004, 4,209,744, 4,380,931 and 4,480,225 for more complete information.

Returning now to FIG. 1, as mentioned above, the eddy-current tester 22 provides one or more fault signals as indicated by a line 24. The line 24 may include several signal lines including a signal line for indicating major faults and a signal line for indicating minor faults. These are standard outputs on the Forster DEFECTOMAT. The operator is given the opportunity to set the levels which trigger the various fault indications.

Figure 15:
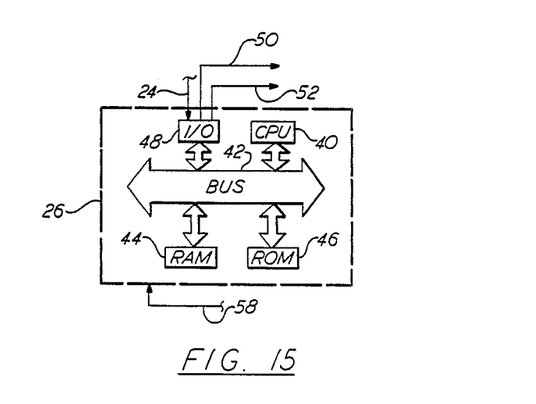
FIG. 15 is an illustration of the signal processor 26 of FIG. 1, including various components typical for signal processors, including that of the signal processor 102.

The signal processor 26 may be a microprocessor such as is well known in the art of electronic signal processing and as is shown in more detail in FIG. 15. There, a central processing unit (CPU) 40 communicates with a bus 42 which may include data, address and control lines. The bus may also communicate with a random access memory (RAM) 44, a read only memory (ROM) 46 and an input/output (I/0) device 48. The signal processor of FIG. 1 responds to the fault signals of FIG. 1 on line 24. The signal processor 26 of FIG. 15 also provides a pair of signals 50, 52, as in FIG. 1, which provide the necessary information signals to a printer 54 and a display 56, respectively. The signal processor 26 of FIG. 15 is also responsive to a power signal on a line 58 which provides power from a power supply 60, shown in FIG. 1, for providing power to the signal processor 26.

Referring back to FIG. 1, the apparatus of the present invention may also include a mass storage device 62 for storing, among other things, fault signals which have been uniquely identified with a particular supplier's rod coil 18 and also with the associated manufactured wire coil 20. The mass storage device may be of any of a variety of types including tape, floppy disk, hard disk, optical, etc. However, tape is usually preferred for its low cost. Other identifiers may also be stored therein to further aid identification and traceability. The identification number placed on mass storage may also be placed on a wire spool after the wire is insulated for delivery to a customer. The number may also be placed on the customer invoice. In this way, customer complaints generated by defective wire may be traced back to a particular supplier's rod coil 18. Other relevant information may also be stored for increased traceability and for quality control purposes.

Figure 14:
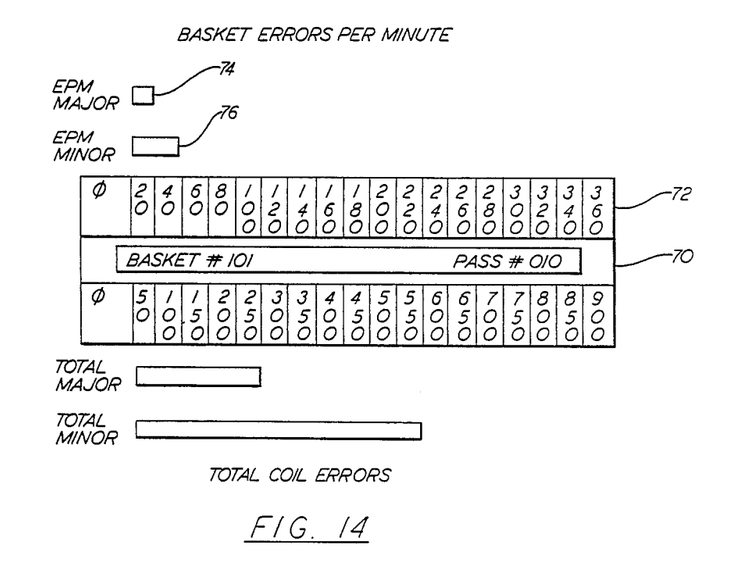
FIG. 14 is an illustration of a display format for the display 56 or printer 54 of FIG. 1.

The display 56 of FIG. 1 may be a CRT display having an informational layout as shown in more detail in FIG. 14. There, a CRT display is shown in a bargraph format. In the center of the display a block 70 is shown indicating which basket and pass number is currently under test. A pass number may indicate the number of minutes which have elapsed since the beginning of the test on a particular coil. The number is incremented at the conclusion of each pass or selected time interval. Normally, a coil is tested in about 35 minutes with the wire travelling at a speed of 25-30 meters per second. Thus, in the illustration of FIG. 14, basket number 101 is being tested and approximately 10 minutes have elapsed since the beginning of the test of this particular coil.

The upper half of the display is devoted to basket errors per minute in two categories: major and minor. The horizontal axis 72 in the upper half of the screen is calibrated in intervals of 20 errors per minute. As will be observed from an EPM major bar 74 of FIG. 14, approximately 20 major errors have occurred in pass number 10 while approximately 40 minor errors have occurred during the same pass, as indicated by an EPM minor bar 76. This means that 20 major errors and 40 minor errors have been detected during the one minute interval currently under test.

The lower half of the screen illustrated in FIG. 14 shows the total coil errors accumulated since the beginning of pass number 1 and up to and including all of the faults detected so far through pass number 10. Of course, the display will be updated with respect to pass number 10 after it is completed. In this case, this will be every minute. A more or less frequent pass interval may of course be selected. As will be observed from the illustration by referring to an axis 78 and a total major coil error bar 80, approximately 250 major errors have been counted while, with reference to a total minor coil error bar 82, approximately 550 minor errors have been counted during the same period.

The bargraph method of presentation shown in FIG. 14 is particularly useful for presenting the operator with a graphic illustration of how fast errors are currently occurring and how many errors have occurred for this particular coil. It is particularly useful to be able to graphically see how fast errors are occurring since a particularly rapid increase in errors in a short period of time may indicate that something is wrong with the rod mill and it perhaps should be shutdown before any serious damage occurs. The level of rate of increase which suggests a shutdown should be initiated may be established by experience.

For a coil which is consistently showing a large number of total coil errors, on the other hand, it may be advantageous to stop using that coil and substitute a new coil at the input to the rod mill so that the spooled wire is not adversely affected by inferior rod stock. This level may also be established by experience.

Figure 2:
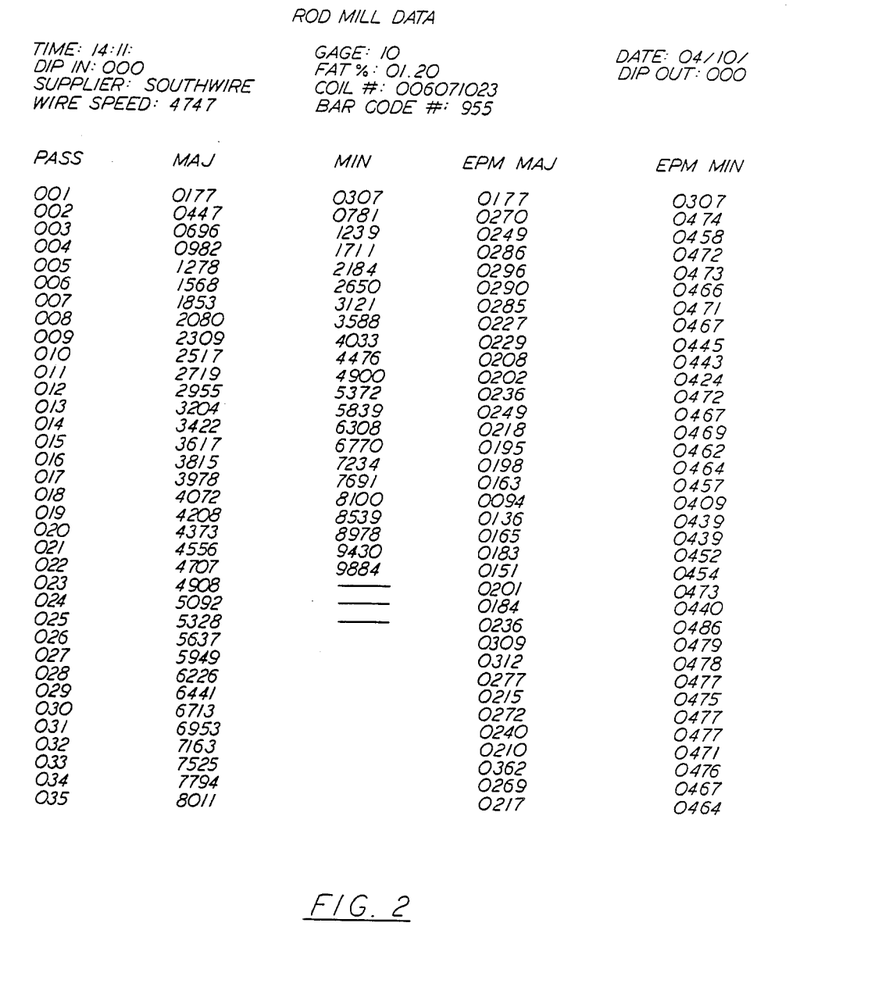
FIG. 2 is an illustration of data in tabular form which may be printed on the printer of FIG. 1.

The printer 54, or even the display 56, of FIG. 1 may present the same information in a tabular format as shown in FIG. 2. Although the absolute numbers are different from those shown in FIG. 14, the type of information is numerically similar. Thus, FIG. 2 has a first column which indicates the pass number. Each pass lines up with a corresponding row in the other four columns. The second and third columns indicate the total number of major and minor faults counted so far for all passes. It will be observed that the minor error column has terminated at pass number 23 which indicates, in this particular case, that a counter limit has been exceeded. This could mean that the coil should be changed.

The fourth and fifth columns indicate the number of major and minor errors on a per minute (per pass) basis. Thus, during pass number 9, there were 229 major errors and 445 minor errors. Similarly, during pass number 22 there were 151 major errors and 454 minor errors. The tabular method shown in FIG. 2 can also be used in a manner similar to that described in FIG. 14 for detecting potential rod mill problems or coil problems. No abnormal rate of increase occurred during the test illustrated in FIG. 2 and therefore neither column 4 nor 5 has terminated.

The hard copy provided by the printer as illustrated in FIG. 2 includes printed data at the top of the sheet including the time, date, gauge wire produced, "dip in" temperature and "dip out" temperature, fat percent, supplier, coil number, wire speed and a bar code. All of this information may be stored, along with the error and pass information in the mass storage unit 62 of FIG. 1. The bar code number uniquely identifies the spool upon which the wire is ultimately coiled for delivery to a customer. The customer is given the bar code number and uses that number for identifying any problem spools received.

The apparatus 10 of the present invention, as shown in FIG. 1, may also include the provision of fault signals on a line 100 to another signal processor 102 which serves a control, rather than a monitoring function such as is performed by the signal processor 26. Of course, as is well known in the signal processing art, any one signal processor such as signal processor 26 in FIG. 1 can accomplish both monitoring and control function tasks. The signal processors 26, 102 are shown separately in FIG. 1 primarily as a conceptual aid to help distinguish the monitoring from the control functions of the present invention. It should be understood, however, that the control and monitoring functions may be combined in a single signal processor such as signal processor 26. Alterntively, the functions may be separated as shown in FIG. 1. The signal processor 102 and the signals associated with it are shown in dashed lines to indicate that it is optional to include the control function and, if included, it may be embodied in a separate signal processor 102 or may instead be incorporated in signal processor 26.

The control function provided by the present invention is to quantitatively detect a rate of increase in detected errors which exceeds an acceptable maximum rate of increase. If exceeded, a shutdown signal on a line 104 is provided to the rod mill 12 which effectuates shutdown of the rod mill until the problem which created the unacceptable rate of increase can be corrected.

The signal processor 102 may also keep track of the total number of counted errors accumulated for a particular coil during all passes. If a selected maximum acceptable level is exceeded, a "change coil" message may be sent on a line 106 to the printer 54 or the display 56. In this way, the operator can take action to remove a defective coil 18 and substitute a new coil at the input of the rod mill. Although this is not a true "control" function it is included here because it is akin to one in that a similar comparison of a count is made and a decision is made to send a message to the operator directly leading to a response on his part.

Figure 13:
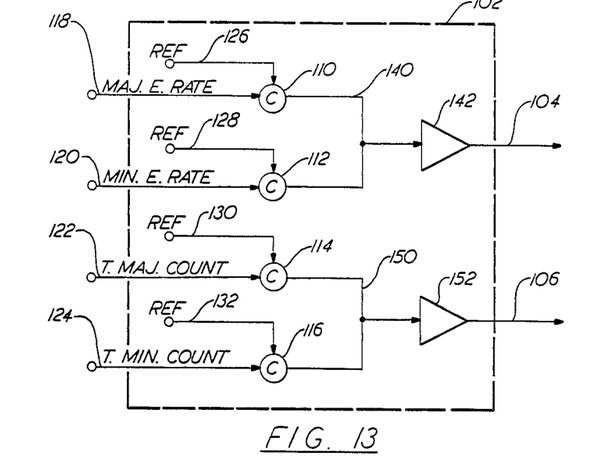
FIG. 13 is a system level illustration of the control and display functions accomplished by the signal processor 102 of FIG. 1.

Referring now to FIG. 13, the claimed method may be conceptually illustrated by a systems level diagram of the signal processor 26 of FIG. 1. The illustration of FIG. 13 shows a number of comparators 110, 112, 114, 116 for comparing the magnitudes of various signals 118, 120, 122, 124, respectively, to a corresponding plurality of respective reference signal magnitudes on lines 126, 128, 130, 132. The signals on lines 118, 120 are indicative of, respectively, the present rate of increase of major and minor errors. If the major error rate signal on line 118 exceeds the reference signal level on line 126 a shutdown signal is provided on a line 140 to an amplifier 142 which in turn provides an amplified shutdown signal on the line 104 for shutting down the rod mill 12 of FIG. 1. Similarly, if the minor error rate signal on line 120 exceeds the reference signal level on line 128 a shutdown signal on line 140 is also sent to amplifier 142 for amplification and provision on line 104 to the rod mill for effecting shutdown.

The signal on line 122 is indicative of the totalized major fault count and is compared in the comparator 114 to a selected totalized major fault count beyond which is considered unacceptable. If that level is exceeded a message signal is provided on a line 150 to an amplifier 152 which provides the "change coil" message signal on line 106 for the printer 54 and/or display 56 of FIG. 1.

Similarly, if the magnitude of the totalized minimum count signal on line 124 exceeds a selected level as indicated, by a reference signal on a line 132, the comparator 116 provides the message signal on line 150 as well and the printer and/or display provides a "change coil" message. Of course, it will be understood that the signals 118, 120, 122, and 124 are shown generically by the signal line 100 in FIG. 1.

As mentioned previously, all of these functions will normally be accomplished on a digital signal processor 26 as illustrated in FIG. 15. As also previously mentioned, the monitoring and control functions can be unified in a single signal processor 26 or may be split functionally between two signal processors 26, 102. It is even conceivable that more than two signal processors could be utilized in a complex control environment. It will be understood that the scope of the present invention is not limited to any particular number of signal processors.

The flow chart illustrations of FIGS. 3, 4, 5, 6, 7, 8, 9, 10 and 11 are illustrative of the logical steps which may be accomplished in the signal processor 26 of FIG. 15 and FIG. 1 in conjunction with a second signal processor 102, if desired, as shown in FIG. 1 to accomplish the objects of the present invention.

Figure 3:
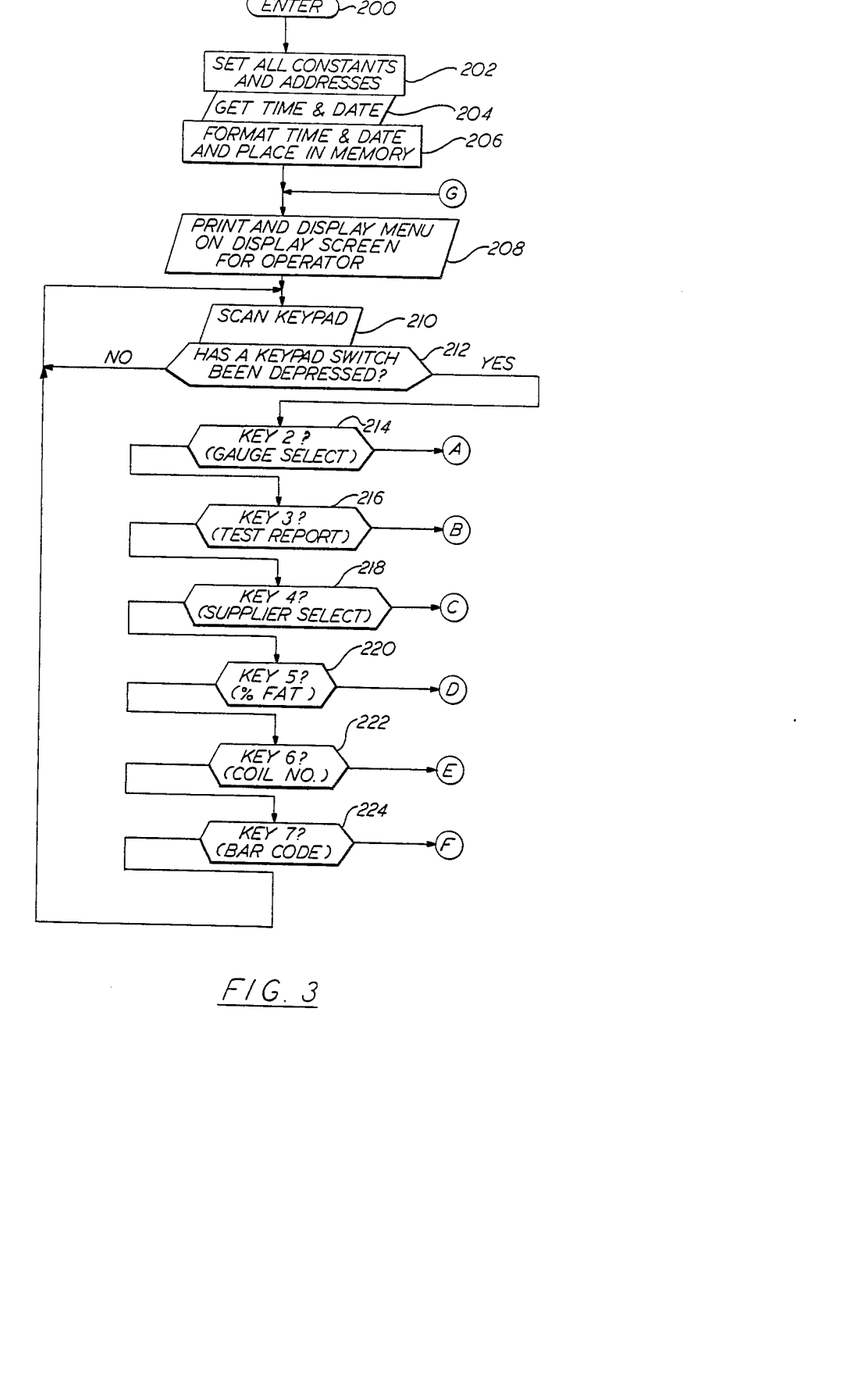
FIG. 3 is a flow chart illustration of the logical steps which may be carried out by the signal processor 26 of FIG. 1.

Referring now to FIG. 3, a flow chart illustration is there presented of a series of logical steps which may be taken on a signal processor 26, as shown in FIG. 1. The flow chart illustrations of FIGS. 4, 5, 6, 7, 8, 9 and 10, it will be understood, are associated with FIG. 3 and are to be read in conjunction therewith.

After entering at a step 200, a step 202 is next executed in which all constants and addresses are set. A step 204 is next executed in which the present time and date are obtained from a free running clock and calendar (not shown in FIG. 1). A step 206 is next executed in which the time and date information is formatted and placed in memory for later use.

A step 208 is next executed in which a top level menu is displayed on display 56 for the operator's use. Using the top level menu, the operator may enter various pieces of data and select various options to be described below.

Once the menu is displayed, a key pad associated with the signal processor 26 of FIG. 1 is scanned as indicated by a step 210 in order to enable a determination in a step 212 as to whether a key pad switch has been depressed or not. If not, a return to step 210 is made until such a key pad switch depression is detected. Once detected, a determination must be made in a series of steps 214, 216, 218, 220, 222, and 224 as to which key has been depressed.

Figures 4, 5:
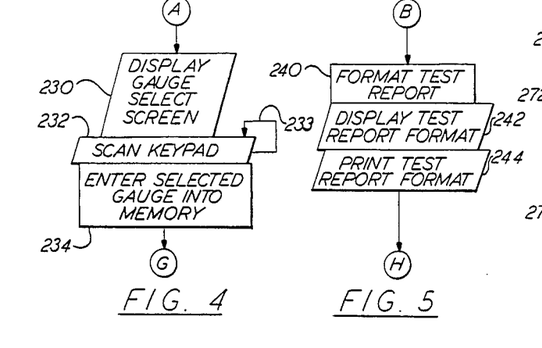
FIG. 4 is a subroutine for displaying a gauge select menu for enabling the operator to enter a selected gauge into the signal processor 26 memory.
FIG. 5 is a simplified flow chart illustration of the steps required to display the test report formats on the display and printer of FIG. 1.

If a determination is made in step 214 that an arbitrarily designated key number 2 (gauge select) has been depressed, a subroutine illustrated in FIG. 4 is next executed.

Referring now to FIG. 4, that indicates, in this case, that key number 2 is associated with a desire on the part of the operator to enter the gauge of the flexible wire presently being fabricated by the rod mill. Therefore, the depression of key pad switch number 2 causes a gauge select menu screen to be displayed on the display 56 as indicated by a step 230. The key pad is repeatedly scanned, as indicated in step 232 by a loop 233 until a selected gauge has been entered by the operator. Once entered, the selected gauge is stored in memory, as indicated by a step 234 and a return is then made to the logical steps of FIG. 3 in such a manner that step 208 is next executed so that additional information or options may be selected by the operator.

If, instead, key 3 had been depressed, as determined in a step 216, a subroutine illustrated in FIG. 5 would next have been executed. Referring now to FIG. 5, the depression of key 3 would indicate that the operator desires a test report to be printed on printer 54 and displayed on display 56 of FIG. 1. This key number 3 would normally be the last to be depressed, after entering all the relevant information. A step 240 formats the test report which is displayed as executed by step 242 and printed by step 244. A transition is then made to a subroutine illustrated in FIG. 10 in which eddy-current fault information is continually gathered for the test report printout and display.

Figure 10:
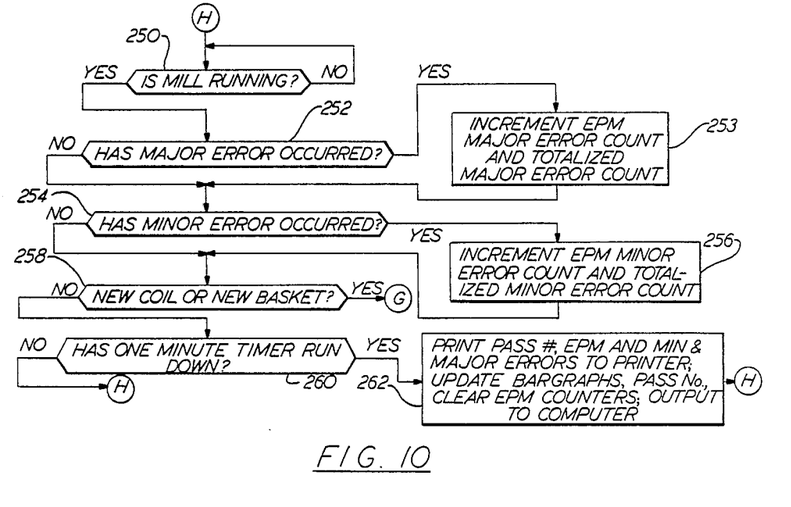
FIG. 10 is a simplied flow chart illustration of logical steps which may be performed in order to keep track of major and minor error signals which have been provided by the eddy-current tester.

Referring now to FIG. 10, a step 250 is first executed in which a determination is made as to whether or not the rod mill is running. If not, step 250 is reexecuted repeatedly until a determination is made that it is. If the determination is in the affirmative a step 252 is next executed in which a determination is made as to whether or not a major error has occurred. If so, the major error per minute count and the totalized major error count are both incremented by one as indicated by a step 253 and a step 254 is next executed in which a determination is made as to whether or not a minor error has occurred. If no major error had been detected in step 252, step 254 would have been executed directly rather than executing step 253 first.

If a minor error has been detected in step 254, a step 256 is next executed in which the minor error per minute and the totalized minor error counts are both incremented. A step 258 is next executed in which a determination is made as to whether or not a new coil or new basket has just been put on line. If the determination of step 254 had been in the negative, step 256 would not have been executed and step 258 would have been executed directly.

If step 258 determines that a new coil or new basket has just been added, a return is made to the program of FIG. 3 such that step 208 is next exeucted and all of the information required for a new coil or new basket can be entered properly before displaying a test report.

If no new coil or new basket is determined to be present in step 258, a step 260 is next executed in which a determination is made as to whether or not an associated one minute timer has run down. If not, a return is made to the beginning of the subroutine illustrated in FIG. 10 at step 250. This would indicate that the particular pass being monitored has not yet finished. If it has finished, then the one minute timer has run down and the next step executed would be a step 262 in which a printout and display is made of the particular pass presently being finished off. In FIG. 2 this would mean that, e.g., if pass number 5 had just been completed then a printout of that line would be made indicating that 1,278 major faults, 2,184 minor faults, had been totalized so far in the first 5 passes, and that 296 major errors per minute had occurred during pass 5 and that 473 minor errors had occurred during pass 5. Similarly, a bargraph display similar to that illustrated in FIG. 14 would be displayed on the display 56 of FIG. 1 showing that pass number 5 had just been completed and incrementing the bargraphs accordingly. The pass number storage registers and EPM counters would be cleared and the information would be stored in the mass storage unit 62 illustrated in FIG. 1 for later reference.

After step 262 is executed, a return will be made to the beginning of the logical steps illustrated in FIG. 10. The only way to exit the steps illustrated in FIG. 10 is to start a new coil or new basket via step 258.

Figure 6:
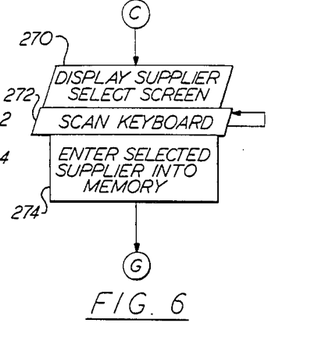
FIG. 6 is a subroutine associated with FIG. 3 whereby the operator is enabled via a supplier select menu to enter the coil supplier into memory.

Referring back to FIG. 3, if it is determined in the step 218 that key 4 has been depressed, then a branch to a subroutine illustrated in FIG. 6 is made in which a series of steps, beginning with a step 270 are made. In step 270, a supplier-select screen menu is displayed in which the name of one specific supplier of the various suppliers of copper rod coils may be entered. A step 272 is next executed in which the key pad is scanned until the supplier's name has been entered or selected. Step 274 is next executed in which the selected supplier's name is entered into memory. A return is then made to the main program illustrated in FIG. 3 and step 208 is next executed.

Figure 7:
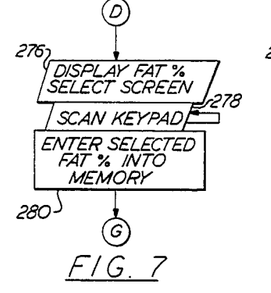
FIG. 7 is a subroutine associated with the logical steps of FIG. 3 whereby the operator is enabled by means of a fat percent select menu to enter the present percent fat into memory.

If it is determined in step 220 of FIG. 3 that key 5 has been depressed then a branch is made to a subroutine illustrated in FIG. 7 in which a step 276 is next executed in which a fat percent display select screen is presented on the CRT display. A step 278 is next executed in which the key pad is scanned in order to detect the operator depressing the percent fat presently in the system. Once the key or keys are selected, the selected percent fat is entered into memory in a step 280. A return is then made to the main program and step 208 is next executed again.

Figure 8:
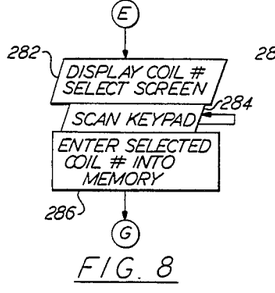
FIG. 8 is a simplified flow chart illustration of steps which may be executed in order to display a coil number entry menu by which the operator is enabled to enter the coil number for storage in memory.

If it is determined by a step 222 of FIG. 3 that key 6 has been depressed, a branch is made to a subroutine illustrated in FIG. 8 in which a step 282 is first exeucted in order that a display coil number select screen may be presented on the CRT. A step 284 is next executed in which the key pad is scanned to determine if the operator has entered a coil number. If so, a step 286 is next executed in which the selected coil number is entered into the signal processor's memory. A return is then made to the program illustrated in FIG. 3 at step 208.

Figure 9:
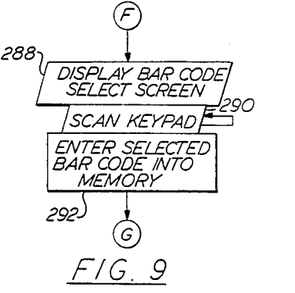
FIG. 9 is a flow chart illustration of a series of steps which may be executed to display a bar code select menu for enabling the operator to select a bar code for storage in memory.

If it has been determined in step 224 of FIG. 3 that key number 7 has been depressed by the operator, a branch is made to a subroutine illustrated in FIG. 9 where a step 288 is first executed in which a bar code display select screen is presented on the CRT for use by the operator in entering a bar code number which is used to uniquely identify the wire provided by the rod mill. A step 290 is next executed in which the key pad is scanned to detect entry of a bar code number by the operator. Once the complete bar code is entered it is stored in the signal processor's memory in a step 292. A return is then made to the program illustrated in FIG. 3 at step 208.

Figure 11:
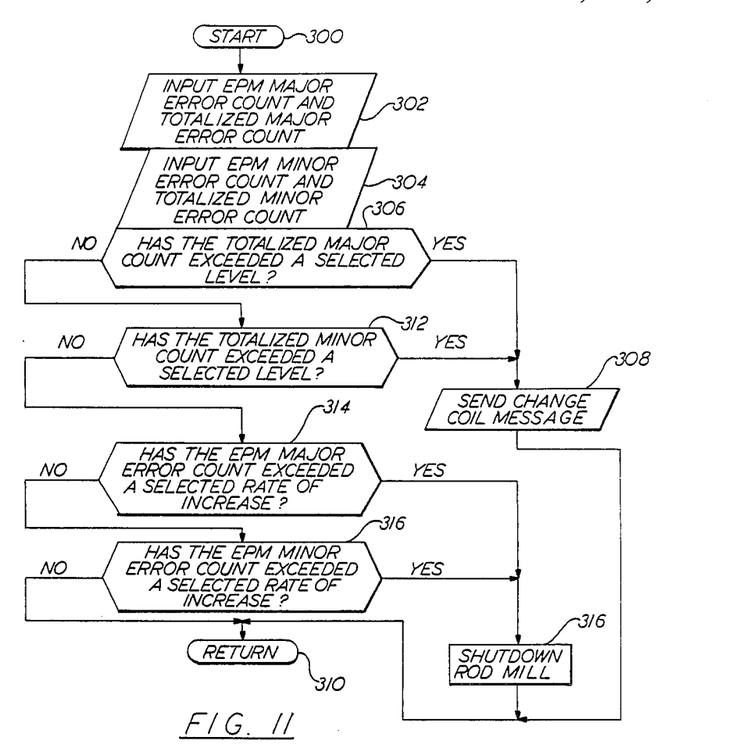
FIG. 11 is a simplified flow chart illustration of a number of steps which may be, for example, executed by the signal processor 102 of FIG. 1 in carrying out the control function of shutting down the rod mill in the presence of a rate of increase of error signals greater than a selected maximum rate of increase and for providing a displayed message to the operator indicative of the need to replace the present coil 18 due to it being deemed defective in the presence of a total fault count greater than a selected level.

Referring now to FIG. 11, a subroutine is there illustrated for use for control purposes, such as would be used by the signal processor 102 of FIG. 12 in determining when to shutdown the rod mill 12 or when to send a "change coil" message to the display 56 and to the printer 54. Beginning with a start step 300, a step 302 is next executed in which the EPM major error count and the totalized major error count are input via signal line 100 of FIG. 1. A step 304 is next executed in which EPM minor error count and totalized minor error count are similarly input to the signal processor 102. A step 306 next determines whether the totalized major count has exceeded a selected level. If so, a "change coil" message is output on signal line 106 of FIG. 1 as indicated by a step 308. A return is then made via a step 310. If step 306 determines that the selected level has not been exceeded by the totalized major error count, then a step 312 is next executed in which a determination is made as to whether the totalized minor error count has exceeded a selected level. If so, a similar message is sent via step 308 to the CRT display 56 of FIG. 1 and to the printer, if desired. If the totalized minor error count has not exceeded the selected level, a step 314 is instead executed in which a determination is made as to whether or not the EPM major error count has exceeded a selected rate of increase. If so, a signal is sent on line 104 to shutdown the rod mill as indicated by a step 316. In that event, a return is made via step 310 to the program illustrated in FIG. 3, i.e., at the enter step 200. Of course, it will be understood that the calculation of a rate of increase for either major or minor counts may be made on a per count basis or on a per interval basis.

If step 314 of FIG. 15 has not indicated that the EPM major error count has exceeded the selected rate of increase, then a step 316 is next executed in which a determination is made as to whether the EPM minor error count has exceeded a selected rate of increase. If so, a shutdown signal is sent on line 104 to the rod mill as indicated by the step 316. If the EPM minor error count has not exceeded the selected rate of increase then a return is made in step 310 to the main program.

Although the invention has been shown and described with respect to a best mode embodiment thereof, it should be understood by those skilled in the art that the foregoing and various other changes, omissions, and additions in the form and detail thereof may be made therein without departing from the spirit and scope of the invention.

We claim:

1. A method of controlling a rod mill for drawing wire from a rod, comprising the steps of:
   eddy-current testing the wire drawn in the rod mill from the rod for providing fault signals in the presence of tested faults in the wire;
   counting the number of fault signals provided on a per unit time basis and providing count signals having magnitudes indicative thereof after each unit time elapses;
   determining the rate of increase of said count signal magnitude and providing a rate of increase signal indicative thereof;
   comparing the magnitude of said rate of increase signal to a reference signal having a selected magnitude; and
   providing a rod mill shutdown signal in response to said rate of increase signal magnitude being greater than said reference signal's magnitude.

2. The method of claim 1, wherein said step of displaying is made in tabular form.

3. The method of claim 1, wherein said step of displaying is made in bargraph form.

4. The method of claim 1, further comprising the steps of:
   counting the number of fault signals provided to provide a totalized count signal having a magnitude indicative of the total number of fault signals provided; and
   displaying the magnitude of said totalized count signal along with said count signal magnitudes.

5. The method of claim 1, further comprising the step of storing said magnitudes of said count signals provided on a per unit time basis for later evaluation.

6. The method of claim 5, further comprising the steps of:
   identifying the supplier of the coil of rod by providing a supplier identifying signal; and
   storing said supplier identifying signal along with said count signal magnitudes.

7. The method of claim 5, further comprising the steps of:
   identifying the percent fat presently in a lubricant sprayed on rod drawing dies in the rod mill by providing a percent fat signal; and
   storing said percent fat signal magnitude along with said count signal magnitudes.

8. The method of claim 5, further comprising the steps of:
   providing a rod coil identifying signal having a magnitude indicative of the identity of the rod coil presently being drawn in the rod mill; and
   storing said rod coil identifying signal along with said count signal magnitudes.

9. The method of claim 1, wherein said fault signals are characterized as either major or minor and wherein said major and minor fault signal magnitudes are counted and displayed separately.

10. The method of claim 1, further comprising the step of displaying said magnitudes of said count signals.

11. The method of claim 4, further comprising the steps of:
    comparing the magnitude of said totalized count signal to a selected signal magnitude; and
    providing a "change coil" signal in the presence of said totalized count signal in the presence said selected signal magnitude.

12. Apparatus for controlling a rod mill for drawing wire from a rod, comprising:
    an eddy-current tester for testing the wire drawn in the rod mill from the rod for providing fault signals in the presence of tested faults in the wire;
    means for counting the number of fault signals provided on a per unit time basis and providing count signals having magnitudes indicative thereof after each unit time elapses;
    means for determining the rate of increase of said count signal magnitude and providing a rate signal indicative thereof;
    means for comparing the magnitude of said rate of increase signal to a signal having a selected magnitude; and
    means for providing a rod mill shutdown signal in the presence of said rate of increase signal magnitude being greater than said signal having a selected magnitude.

13. The apparatus of claim 12, wherein said means for displaying displays the magnitudes of said count signals in tabular form.

14. The apparatus of claim 12, wherein said means for displaying displays the magnitudes of said count signals in tabular form.

15. The apparatus of claim 12, further comprising:
    means for counting the number of fault signals provided to provide a totalized count signal after each unit time elapses each having a magnitude indicative of the total number of faults counted in all previous units of time; and wherein
    said means for displaying displays the magnitudes of said totalized count signals along with said count signal magnitudes.

16. The apparatus of claim 12, further comprising:
    means for storing said magnitudes of said count signals and said totalized count signals for later evaluation.

17. The apparatus of claim 16, further comprising:
    means for identifying the supplier of the coil of rod by providing a supplier identifying signal; and wherein
    means for storing the magnitude of said supplier identifying signal along with said count signal magnitudes.

18. The apparatus of claim 16, further comprising:
    means for identifying the percent fat presently in a lubricant sprayed on rod drawing dies in the rod mill by providing a percent fat signal; and wherein
    means for storing said percent fat signal magnitude along with said count signal magnitudes.

19. The apparatus of claim 16, further comprising:
    means for providing a coil of rod identifying signal having a magnitude indicative of the identity of the coil of rod presently being drawn from the rod mill; and wherein
    said means for displaying displays said coil of rod identifying signal magnitude along with said count signal and said totalized count signal magnitudes.

20. The apparatus of claim 12, wherein said fault signals are characterized as either major or minor and wherein said major and minor fault signals are counted and displayed separately.

21. The apparatus of claim 12, further comprising means for displaying the magnitudes of said count signals.

22. The apparatus of claim 15, further comprising:
means for comparing the magnitude of said totalized count signal to a selected signal magnitude; and
means for providing a "change coil" signal in the presence of said totalized count signal magnitude exceeding said selected signal magnitude.

* * * * *

UNITED STATES PATENT AND TRADEMARK OFFICE
CERTIFICATE OF CORRECTION

PATENT NO. : 4,808,926

DATED : February 28, 1989

INVENTOR(S) : Randall C. Graham et al

It is certified that error appears in the above-identified patent and that said Letters Patent is hereby corrected as shown below:

Col. 3, line 58 "vaules" should be -- values --.

Col. 5, line 23 "4" should be -- 14 --.

Col. 5, line 31 "2" should be -- 22 --.

Col. 11, line 19 "exeucted" should be -- executed --.

Col. 14, Claim 11, line 8 "in the presence" should be canceled and -- magnitude exceeding -- should be substituted.

Signed and Sealed this

Thirtieth Day of April, 1991

Attest:

HARRY F. MANBECK, JR.

Attesting Officer

Commissioner of Patents and Trademarks